United States Patent [19]

Ayer

[11] 4,126,744
[45] Nov. 21, 1978

[54] 4-OXO-PGI$_1$ COMPOUNDS

[75] Inventor: Donald E. Ayer, Kalamazoo, Mich.

[73] Assignee: The Upjohn Company, Kalamazoo, Mich.

[21] Appl. No.: 857,106

[22] Filed: Dec. 5, 1977

[51] Int. Cl.$^2$ ............................................ C07D 307/93
[52] U.S. Cl. .................................... 542/426; 542/429; 544/153; 544/376; 260/326.36; 260/346.22; 260/346.73; 546/196; 546/194; 546/256; 546/269
[58] Field of Search ...................... 260/346.22, 346.73, 260/293.58, 295 K, 326.36; 542/426, 429; 544/153, 376

[56] References Cited
PUBLICATIONS

Pace-Asuak et al., Biochemistry, vol. 10, (20), 1971, pp. 3657-3664.

Primary Examiner—Henry R. Jiles
Assistant Examiner—Bernard Dentz
Attorney, Agent, or Firm—Robert A. Armitage

[57] ABSTRACT

This invention relates to certain structural and pharmacological analogs of 5,6-dihydro-prostacyclin (PGI$_1$) wherein the C-4 position is substituted by oxo. These novel 4-oxo-prostacyclin-type compounds are useful for the same pharmacological purposes as prostacyclin, particularly being smooth muscle stimulators and platelet aggregation inhibitors.

43 Claims, No Drawings

4-OXO-PGI₁ COMPOUNDS

BACKGROUND OF THE INVENTION

This invention relates to novel structural and pharmacological analogs of 5,6-dihydro-prostacyclin (PGI₁). In particular, the present invention relates to prostacyclin-type compounds wherein the C-4 position of prostacyclin is substituted by an oxo.

Prostacyclin is an endogenously produced compound in mammalian species, being structurally and biosynthetically related to the prostaglandins (PG's). In particular, prostaglandin exhibits the following structure and atom numbering:

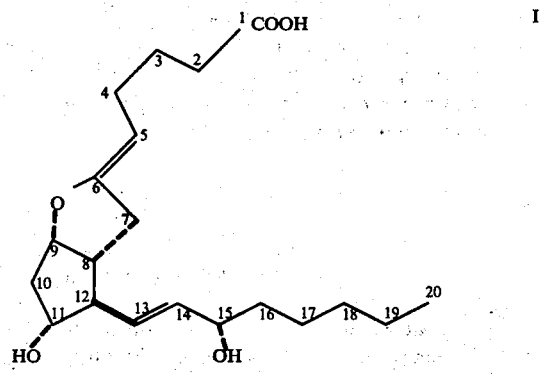

5,6-Dihydroprostacyclin exhibits the following structure and atom numbering:

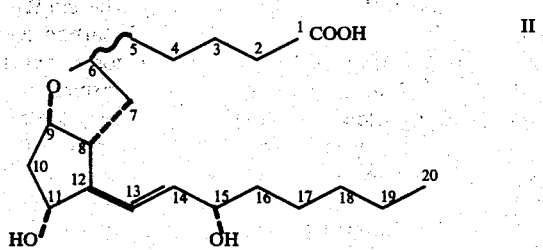

As is apparent from inspection of formula I and II, prostacyclin and 5,6-dihydroprostacyclin (i.e., PGI₁) bear a structural relationship to PGF₂α, which exhibits the following structure and atom numbering:

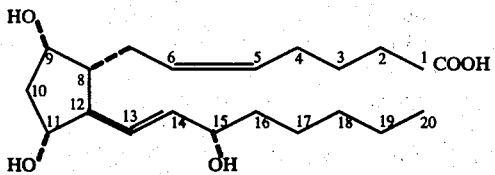

As is apparent by reference to formula III, prostacyclin and 5,6-dihydroprostacyclin may be trivially named as a derivative of PGF-type compounds. Accordingly, prostacyclin is trivially named 9-deoxy-6,9α-epoxy-(5Z)-5,6-didehydro-PGF₁ and 5,6-dihydro prostacyclin is named 9-deoxy-6,9α-epoxy-PGF₁. For description of the geometric stereoisomerism employed above, see Blackwood et al., Journal of the American Chemical Society 90, 509 (1968). Further, for a description of prostacyclin and its structural identification, see Johnson et al., Prostaglandins 12, 915 (1976).

For convenience, the novel prostacyclin analogs described herein will be referred to by the trivial, art-recognized system of nomenclature described by N. A. Nelson, Journal of Medicinal Chemistry, 17, 911 (1974) for the prostaglandins. Accordingly, all of the novel prostacyclin derivatives herein will be named as 9-deoxy-PGF₁-type compounds or alternatively and preferably as PGI₁ or PGI₂ derivatives.

In the formulas above, as well as in formulas hereinafter, broken line attachments to any ring indicate substituents in "alpha" (α) configuration, i.e., below the plane of such ring. Heavy solid line attachments to any ring indicate substituents in "beta" (β) configuration, i.e., above the plane of such ring. The use of wavy lines (∼) herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). See also Nature 212, 38 (1966) for discussion of the stereochemistry of the prostaglandins, which discussion applies to the novel prostacyclin analogs herein. Further, the carboxy-terminated side chain is attached to the heterocyclic ring of PGI in either the alpha or beta configuration, which by the above convention represents the (6R) or (6S) configuration, respectively. Expressions such as C-4, C-15, and the like, refer to the carbon atom in the prostaglandin or prostacyclin analog which is in the position corresponding to the position of the same number in PGF₂α or prostacyclin, as enumerated above.

Molecules of PGI₁, PGI₂, and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the above formula for PGI₂ corresponds to that endogenously produced in mammalian tissues. In particular, refer to the stereoconfiguration at C-8 (alpha), C-9 (alpha), C-11 (alpha), and C-12 (beta) of endogenously-produced prostacyclin. The mirror image of the above formula for prostacyclin represents the other enantiomer. The racemic forms of prostacyclin contains equal numbers of both enantiomeric molecules, and the above formula I and its mirror image is needed to represent correctly the corresponding racemic prostacyclin.

For convenience hereinafter, use of the term prostaglandin ("PG") or prostacyclin ("PGI₂") will mean the optically active form of that prostaglandin or prostacyclin thereby referred to with the same absolute configuration as PGF₂α, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one of the same pharmacological purposes as the prostaglandins or prostacyclin, respectively.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostacyclin analog", as used herein, represents that stereoisomer of a prostacyclin-type product which is of the same relative stereochemical configuration as prostacyclin obtained from mammalian tissues or a mixture comprising that stereoisomer and the enantiomer thereof. In particular, where a formula is used to depict a prostacyclin-type product herein, the term "prostacyclin analog" refers to the compound of that formula or a mixture comprising that compound and the enantiomer thereof.

SUMMARY OF THE INVENTION

The present specification particularly discloses:
a prostacyclin analog of the formula

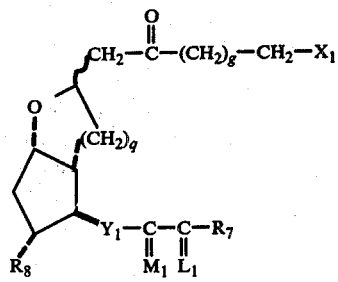

wherein $q$ is the integer one or 2;
wherein $g$ is the integer one, 2, or 3;
wherein $R_8$ is hydrogen, hydroxy, or hydroxymethyl;
wherein $Y_1$ is
(1) trans—CH=CH—,
(2) cis—CH=CH—,
(3) —CH$_2$CH$_2$—, or
(4) —C≡C—,
wherein $M_1$ is

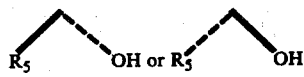

wherein $R_5$ is hydrogen or alkyl with one to 4 carbon atoms, inclusive,
wherein $L_1$ is

or a mixture of

wherein $R_3$ and $R_4$ are hydrogen, methyl, or fluoro, being the same or different, with the proviso that one of $R_3$ and $R_4$ is fluoro only when the other is hydroen or fluoro;
wherein $X_1$ is
(1) —COOR$_1$ wherein $R_1$ is hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

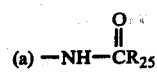

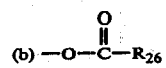

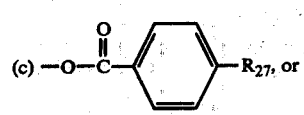

wherein $R_{25}$ is methyl, phenyl, acetamidophenyl, benzamidophenyl, or —NH$_2$; $R_{26}$ is methyl, phenyl, —NH$_2$, or methoxy; and $R_{27}$ is hydrogen or acetamido; inclusive, phenacyl, i.e.,

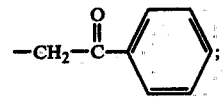

phenacyl substituted in the para position by chloro, bromo, phenyl, or benzamido; or a pharmacologically acceptable cation;
(2) —CH$_2$OH: or
(3) —COL$_4$, wherein L$_4$ is
(a) amino of the formula —NR$_{21}$R$_{22}$; wherein R$_{21}$ and R$_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive, hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro; pyridyl; pyridyl substituted by one, 2, or 3 chloro, alkyl of one to 3 carbon atoms, inclusive, or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms, inclusive, hydroxy, or alkoxy of one to 3 carbon atoms, inclusive; hydroxyalkyl of one to 4 carbon atoms, inclusive; dihydroxyalkyl of one to 4 carbon atoms; and trihydroxyalkyl of one to 4 carbon atoms; with the further proviso that not more than one of R$_{21}$ and R$_{22}$ is other than hydrogen or alkyl;
(b) cycloamino selected from the group consisting of

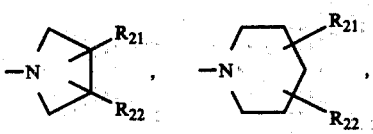

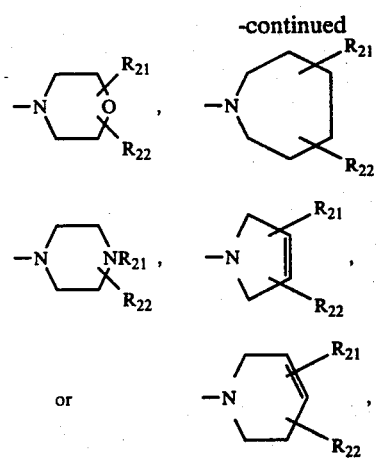

wherein $R_{21}$ and $R_{22}$ are as defined above;

(c) carbonylamino of the formula $-NR_{23}COR_{21}$, wherein $R_{23}$ is hydrogen or alkyl of one to 4 carbon atoms and $R_{21}$ is as defined above;

(d) sulfonylamino of the formula $-NR_{23}SO_2R_{21}$, wherein $R_{21}$ and $R_{22}$ are as defined above; or (e) hydrazino of the formula $-NR_{23}R_{24}$, wherein $R_{23}$ is as defined above and $R_{24}$ is amino of the formula $-NR_{21}R_{22}$, as defined above, or cycloamino, as defined above; and wherein $R_7$ is (1) $-(CH_2)_m-CH_3$,

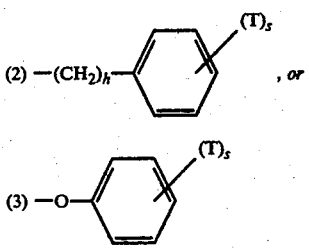

wherein $m$ is the integer one to 5, inclusive, $h$ is the integer zero to 3, inclusive; $s$ is the integer zero, one, 2, or 3, and T is chloro, fluoro, trifluoromethyl, alkyl of one to 3 carbon atoms, inclusive, or alkoxy or one to 3 carbon atoms, inclusive, with the proviso that not more than two T's are other than alkyl.

The novel prostacyclin analogs herein are all named as 4-oxo-PGI$_1$ compounds by virtue of the carbonyl linkage at C-4.

When $q$ is one and $g$ is 2 or 3, the compounds described herein are additionally named as 2a-homo-PGI$_1$-type or 2a,2b-dihomo-PGI$_1$-type compounds, respectively. In this event the additional methylene or ethylene group is considered for the purposes of nomenclature as though it were inserted between the carbon atoms C-2 and C-3. Further, such additional carbon atoms are denoted as C-2a and C-2b, counting from the C-2 to the C-3 carbon atoms, respectively.

When $q$ is two and $g$ is one, 2, or 3, the novel compounds herein are further designated as 7a-homo-PGI$_1$-type, 2a,7a-dihomo- or 2a,2b-7a-trihomo-PGI$_1$-type compounds respectively. In the former case, a methylene group between C-7 and the cyclopentane ring is considered to have been inserted, thereby resulting in the attachment of this ring to C-7a. In the latter cases, the rationale for the nomenclature is as described above for compounds wherein $g$ is two or 3.

The novel prostacyclin analogs herein wherein $R_8$ is hydrogen or hydroxymethyl are respectively referred to as 11-deoxy-PGI$_1$-type or 11-deoxy-11-hydroxymethyl-PGI$_1$-type compounds. Additionally, when $Y_1$ is cis—CH=CH—, —CH$_2$CH$_2$—, or —C≡C—, the novel compounds thereby referred to are named as 13-cis-PGI$_1$-type, 13,14-dihydro-PGI$_1$-type, or 13,14-didehydro-PGI$_1$-type compounds, respectively.

Compounds herein wherein $M_1$ is

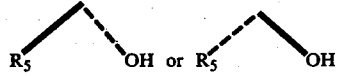

and $R_5$ is alkyl are referred to as 15-alkyl-PGI$_1$-type compounds.

With the exception of the 13-cis-PGI$_1$-type compounds described above, all the above compounds exhibiting a hydroxy or alkoxy moiety in the beta configuration at C-15 are additionally referred to as 15-epi-PGI$_1$-type compounds. For the 13-cis-PGI$_1$-type compounds herein, only compounds exhibiting the hydroxy or alkoxy moiety in the alpha configuration at C-15 are referred to as 15-epi-PGI$_1$-type compounds. The rationale for this system of nomenclature with respect to the natural and epimeric configurations at C-15 is described in U.S. Pat. No. 4,016,184, issued April 5, 1977.

When $R_7$ is $-(CH_2)_m-CH_3$, wherein $m$ is as defined above, the novel compounds herein are named as 19,20-dinor-PGI$_1$-type 20-nor-PGI$_1$-type, 20-methyl-PGI$_1$-type or 20-ethyl-PGI$_1$-type compounds when $m$ is one, 2, 4, or 5, respectively.

When $R_7$ is

wherein T and $s$ are as defined above, and neither $R_3$ nor $R_4$ is methyl, the novel compounds herein are named as 16-phenyl-17,18,19,20-tetranor-PGI$_1$-type compounds, when $s$ is zero. When $s$ is one, 2, or 3, the corresponding compounds are named as 16-(substituted phenyl)-17,18,19,20-tetranor-PGI$_1$-type compounds. When one and only one of $R_3$ and $R_4$ is methyl or both $R_3$ and $R_4$ are methyl, then the corresponding compounds wherein $R_7$ is as defined in this paragraph are named as 16-phenyl- or 16-(substituted phenyl)-18,19,20-trinor-PGI$_1$-type; or 16-methyl-16-phenyl- or 16-methyl-16-(substituted phenyl)-18,19,20-trinor-PGI$_1$-type compounds, respectively.

When $R_7$ is

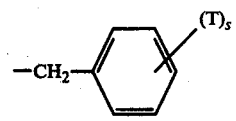

wherein T and $s$ are as defined above, the novel compounds herein are named as 17-phenyl-18,19,20-trinor-PGI$_1$-type compounds, when $s$ is zero. When $s$ is one, 2, or 3, the corresponding compounds are named as 17-(substituted phenyl)-18,19,20-trinor-PGI$_1$-type compounds.

When R7 is

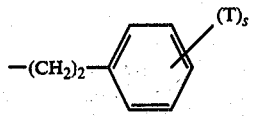

wherein T and s are as defined above, the novel compounds herein are named as 18-phenyl-19,20-dinor-PGI$_1$-type compounds, when s is zero. When s is one, 2, or 3, the corresponding compounds are named as 18-(substituted phenyl)-19,20-dinor-PGI$_1$-type compounds.

When R7 is

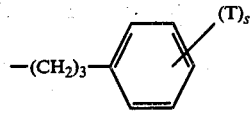

wherein T and s are as defined above, the novel compounds herein are named as 19-phenyl-20-nor-PGI$_1$-type compounds, when s is zero. When s is one, 2, or 3, the corresponding compounds are named as 19-(substituted phenyl)-20-nor-PGI$_1$-type compounds.

When R7 is

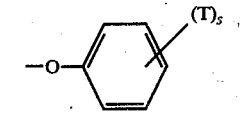

wherein T and s are as defined above, and neither R$_3$ nor R$_4$ is methyl, the novel compounds herein are named as 16-phenoxy-17,19,19,20-tetranor-PGI$_1$-type compounds, when s is zero. When s is one, 2, or 3, the corresponding compounds are named as 16-(substituted phenoxy)-17,19,19,20-tetranor-PGI$_1$-type compounds. When one and only one of R$_3$ and R$_4$ is methyl or both R$_3$ and R$_4$ are methyl, then the corresponding compounds wherein R$_7$ is as defined in this paragraph are named as 16-phenoxy- or 16-(substituted phenoxy)-18,19,20-trinor-PGI$_1$-type compounds or 16-methyl-16-phenoxy- or 16-(substituted phenoxy)-18,19,20-trinor-PGI$_1$-type compounds, respectively.

When at least one of R$_3$ and R$_4$ is not hydrogen then (except for the 16-phenoxy or 16-phenyl compounds discussed above), there are thusly described the 16-methyl-PGI$_1$-type (one and only one of R$_3$ and R$_4$ is methyl), 16,16-dimethyl-PGI$_1$-type (R$_3$ and R$_4$ are both methyl), 16-fluoro-PGI$_1$-type (one and only one of R$_3$ and R$_4$ is fluoro), and 16,16-difluoro-PGI$_1$-type (R$_3$ and R$_4$ are both fluoro) compounds. For those compounds wherein R$_3$ and R$_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When X$_1$ is —CH$_2$OH, the novel compounds herein are named as 2-decarboxy-2-hydroxymethyl-PGI$_1$-type compounds.

When X$_1$ is —COL$_4$, the novel compounds herein are named as PGI$_1$-type, amides. Further when X$_1$ is —COOR$_1$, the novel compounds herein are named as PGI$_1$-type, esters and PGI$_1$-type, salts when R$_1$ is not hydrogen.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

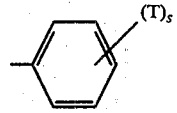

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-trimethylphenyl, (o-, m-, p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-methoxyphenyl, (o-, m-, or p-)ethoxyphenyl, (4- or 5-)chloro-2-methoxyphenyl, and 2,4-dichloro(5- or 6-)methylphenyl.

Examples of phenyl esters substituted in the para position (i.e., X$_1$ is —COOR$_1$; R$_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel prostacyclin amides herein (i.e., X$_1$ is COL$_4$) include the following:

(1) Amides within the scope of alkylamino groups of the formula —NR$_{21}$R$_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopehtylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-methyl-N-cyclohexylamide, dicyclopentylamide, and dicyclohexylamide. Amides within the scope of aralkylamino are benzylamide, 2-phenylethylamide, 2-phenylethylamide, N-methyl-N-benzylamide, and dibenzylamide. Amides within the scope of substituted phenylamido are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are $\alpha$-pyridylamide, $\beta$-pyridylamide, and $\gamma$-pyridylamide. Amides within the scope of substituted pyridylamino are 4-methyl-$\alpha$-pyridylamide, 4-methyl-$\beta$-pyridylamide, 4-chloro-$\alpha$-pyridylamide, and 4-chloro-$\beta$-pyridylamide. Amides within the scope of pyridylalkylamino are $\alpha$-pyridylmethylamide, $\beta$-pyridylmethylamide, $\gamma$-pyridylmethylamide, $\alpha$-pyridylethylamide, $\beta$-pyridylethylamide, $\gamma$-pyridylethylamide, $\alpha$-pyridylpropylamide, $\beta$-pyridylpropylamide, $\gamma$-pyridylpropylamide, $\alpha$-pyridylbutylamide, $\beta$-pyridylbutylamide, and $\gamma$-pyridylbutylamide. Amides within the scope of substituted pyridylalkylamino are 4-methyl-$\alpha$-pyridylmethylamide, 4-methyl-$\beta$-pyridylmethylamide, 4-chloro-$\alpha$-pyridylmethylamide, 4-chloro-$\beta$-pyridylmethylamide, 4-methyl-$\alpha$-pyridylethylamide, 4-methyl-$\beta$-pyridylethylamide, 4-chloro-$\alpha$-pyridylethylamide, 4-chloro-$\beta$-pyridylethylamide, 4-methyl-$\alpha$-pyridylpropylamide, 4-methyl-$\beta$-pyridylpropylamide, 4-chloro-$\alpha$-pyridylpropylamide, 4-chloro-$\beta$-pyridylpropylamide, 4-methyl-$\alpha$-pyridylbutylamide, 4-methyl-$\beta$-pyridylbutylamide, 4-chloro-$\alpha$-pyridylbutylamide, and 4-chloro-$\beta$-pyridylbutylamide. Amides within the scope of hydroxyalkylamino are hydroxymethylamide, $\alpha$-hydroxyethylamide, $\beta$-hydroxyethylamide, $\alpha$-hydroxypropylamide, $\beta$-hydroxypropylamide, $\gamma$-hydroxypropylamide, 1-(hydroxymethyl)ethylamide, 1-(hydroxymethyl)propylamide, (2-hydroxyethyl)propylamide, and $\alpha,\alpha$-dimethyl-$\beta$-hydroxyethylamide. Amides within the scope of dihydroxyalkylamino are dihydroxymethylamide, $\alpha,\alpha$-dihydroxyethylamide, $\alpha,\beta$-dihydroxyethylamide, $\beta,\beta$-dihydroxyethylamide, $\alpha,\alpha$-dihydroxypropylamide, $\alpha,\beta$-dihydroxypropylamide, $\alpha,\gamma$-dihydroxypropylamide, $\beta,\beta$-dihydroxypropylamide, $\beta,\gamma$-dihydroxypropylamide, $\gamma,\gamma$-dihydroxypropylamide, 1-(hydroxymethyl)2-hydroxyethylamide, 1-(hydroxymethyl)1-hdroxyethylamide, $\alpha,\alpha$-dihydroxybutylamide, $\alpha,\beta$-dihydroxybutylamide, $\alpha,\gamma$-dihydroxybutylamide, $\alpha,\delta$-dihydroxybutylamide, $\beta,\beta$-dihydroxybutylamide, $\beta,\gamma$-dihydroxybutylamide, $\beta,\delta$-dihydroxybutylamide, $\gamma,\gamma$-dihydroxybutylamide, $\gamma,\delta$-dihydroxybutylamide, $\delta,\delta$-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula —$NR_{23}COR_{21}$ are methylcarbonylamide, ethylcarbonylamide, phenylcarbonylamide, and benzylcarbonylamide. Amides within the scope of sulfonylamino of the formula —$NR_{23}SO_2R_{21}$ are methylsulfonylamide, ethylsulfonylamide, phenylsulfonylamide, p-tolylsulfonylamide, benzylsulfonylamide.

(4) Hydrazides within the scope of the above hydrazino groups are hydrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine.

The term "pharmacologically acceptable cation" refers to those pharmacologically acceptable salts of the prostacyclin-type carboxylic acids ($X_1$ is —COOH) described above which are conventionally employed with prostaglandins. In particular, such pharmacologically acceptable acceptable salts include pharmacologically acceptable metal cations, amine cations, and quarternary amonium cations. Additionally basic amino acids such as arginine and lysine are employed. Further, certain amine cations such as THAM [tris(hydroxymethyl)amino methyl] and adamanamine are especially useful for the present purposes. Additionally, U.S. Pat. No. 4,016,184, issued Apr. 5, 1977 (particularly column 29), describes salts which are likewise preferred for the present purposes.

The novel prostacyclin analogs disclosed herein produce prostacyclin-like physiological responses.

Accordingly, the novel prostacyclin analogs disclosed herein are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds have useful application as smooth muscle stimulators, antithrombotic agents, antiulcer agents, antiasthma agents, and antidermatosis agents, as indicated below.

(a) Smooth Muscle Stimulation

The novel prostacyclin analogs herein are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

(b) Platelet Aggregation Inhibition.

These novel prostacyclin analogs are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The preferred dosage form for these compounds is oral, although other non-parenteral routes (e.g., buccal, rectal, sublingual) are likewise employed in preference to parenteral routes. Oral dosage forms are conventionally formulated (tablets, capsules, et cetera) and administered 2 to 4 times daily. Doses in the range of about 0.05 to 100 mg./kg. of body weight per day are effective.

The addition of these compounds to whole blood provides in vitro applications such as, storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 μg/ml. of whole blood.

(c) Gastric Secretion Reduction

These novel prostacyclin analogs are also useful in mammals, including man and certain useful animals, e.g., dogs and pigs, to reduce and control gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg. to about 20 μg. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Preferably, however, the novel prostacyclin analogs are administered orally or by other non-parenteral routes. As employed orally, one to 6 administrations daily in a dosage range of about 1.0 to 100 mg./kg. of body weight per day is employed. Once healing of the ulcers has been accomplished the maintenance dosage required to prevent recurrence is adjusted downward so long as the patient or animal remains asymptomatic.

(d) NOSAC-Induced Lesion Inhibition

These novel prostacyclin analogs herein are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly these novel prostacyclin analogs herein are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

(e) Bronchodilation (Antiasthma)

These novel prostacyclin analogs are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostacyclin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament of form about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as ethyl alcohol. Suitable means to employ the aerosol inhalation therapy technique are described fully in U.S. Pat. No. 2,868,691, for example.

(f) Dermatosis Reversal

These novel prostacyclin analogs are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness and noticeably, but incompletely cleared, or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compound, as the active ingredients, constitute from about 0.1% to about 15% by weight of the composition, preferably from about 0.5% to about 2%. In addition to topical administration, injection may be employed, as intradermally, intra- or peri-lesionally, or subcutaneously, using appropriate sterial saline compositions.

Within the scope of the novel prostacyclin analogs described above, certain compounds are preferred in that they exhibit increased potency, selectivity of action, or otherwise represent especially convenient and useful agents.

Accordingly, preferred compounds are those wherein $q$ is the integer one. Further, $g$ is preferably the integer one or 3, most preferably being one. With respect to the $Y_1$ moiety, preferred compounds are those wherein $Y_1$ is trans—CH=CH— or —CH$_2$CH$_2$—, the most especially preferred compounds being those wherein $Y_1$ is trans—CH=CH—. With respect to the $M_1$ moiety, preferred compounds are those wherein $M_1$ is

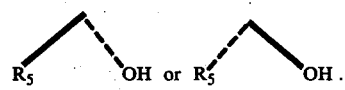

$R_5$ is preferably hydrogen, methyl, or ethyl, most preferably being hydrogen or methyl.

With respect to the $L_1$ moiety, those compounds wherein $R_3$ and $R_4$ are the same are preferred. Further preferred are those compounds herein wherein at least one of $R_3$, $R_4$, and $R_5$ is hydrogen. In the event $Y_1$ is cis—CH=CH— or —C≡C—, compounds wherein $R_3$, $R_4$, and $R_5$ are all hydrogen are preferred.

With respect to the integers $m$, $h$, and $s$, it is preferred that $m$ be the integer 3, $h$ be the integer zero or one and $s$ be the integer zero or one. Further, T is preferably chloro, fluoro, or trifluoromethyl.

Further preferred are the carboxylic acids or derivatives, i.e., esters, especially the p-substituted phenyl esters, and amides. With respect to the novel amides herein, preferred compounds are those wherein $R_{21}$ and $R_{22}$ are preferably hydrogen or alkyl of one to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further, $R_{23}$ is preferably hydrogen.

The chart herein describes the method by which the novel prostacyclin analogs herein are prepared from known or readily synthesized starting materials.

With respect to this chart, g, q, $L_1$, $M_1$, $X_1$, $Y_1$, $R_7$, and $R_8$ are as defined above.

$R_{18}$ is $-OR_{10}$, $-CH_2OR_{10}$, or hydrogen, wherein $R_{10}$ is a readily acid hydrolyzable blocking group such as tetrahydrofuranyl or tetrahydropyranyl. For examples of blocking groups especially contemplated by the present invention see U.S. Pat. No. 4,016,184, issued Apr. 5, 1977. $R_{19}$ is $-Si(G_1)_3$, silyl groups, particularly those described in U.S. Pat. No. 4,016,184. For the purposes of the present invention stable silyl groups such as t-butyldimethylsilyl are especially contemplated.

$M_6$ is

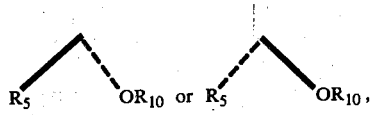

wherein $R_5$ and $R_{10}$ are as defined above.

$Y_2$ is trans—CH=CH—, cis—CH=CH—, —$CH_2CH_2$—, or trans—CH=C(Hal), wherein Hal is chloro, bromo, or iodo.

With respect to Chart A a method is provided whereby the novel prostacyclin analogs of formula XXVI are prepared.

The various formula XXI compounds employed as starting materials in the present synthesis are conveniently prepared from known or readily available starting materials. Formula XXI encompasses compounds deoxygenated at the latent C-11 (for preparing 11-deoxy-$PGI_1$-type compounds) or substituted at the latent C-11 by an hydroxymethyl in place of the hydroxy (for preparing 11-deoxy-11-hydroxymethyl-$PGI_1$-type compounds). These compounds are prepared by methods known in the art from the corresponding 11-deoxy- or 11-deoxy-11-hydroxymethyl-PG's. When q is two, the formula XXI compounds are those known in the art as intermediates for corresponding cis-4,5-didehydro-PG's. Thus, all of the various compounds within the scope of formula XXI represent either known prostaglandin analogs or can be readily prepared by employment of conventional chemical reactions on known prostaglandin type starting materials.

CHART A

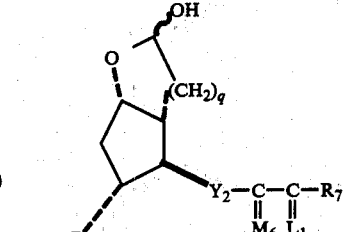

XXI

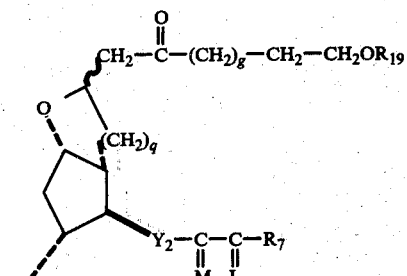

XXII

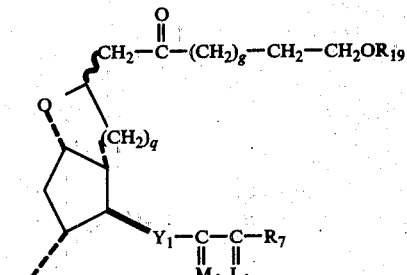

XXIII

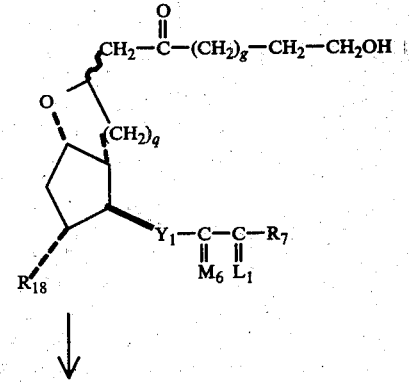

XXIV

-continued
CHART A

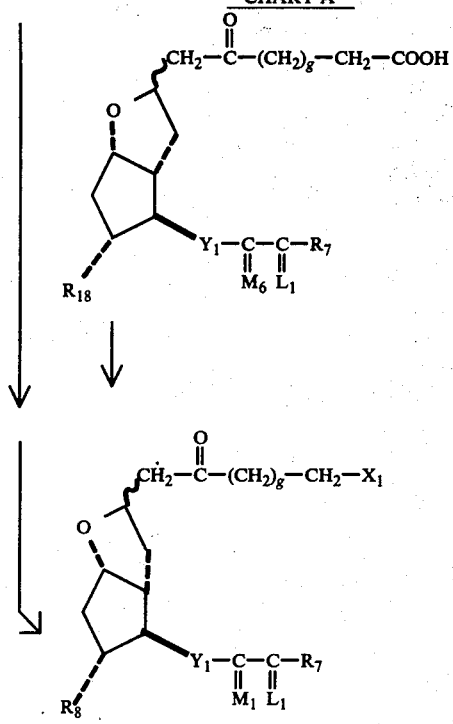

The formula XXII compound is prepared from the formula XXI compound by an Emmons condensation, employing a phosphonate ester of the formula

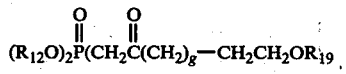

wherein $R_{12}$ is alkyl of one to 4 carbon atoms, inclusive, and $R_{19}$ is as defined above. The phosphonate esters described above are prepared by methods known in the art or are themselves known in the art.

Accordingly, the Emmons condensation proceeds by first reacting the phosphonate with an equal molar amount of an activating agent (e.g., sodium hydride) at 0°–25° C. and thereafter reacting the activated phosphonate reagent with the formula XXI compound. The formula XXII product is then isolated from the reaction mixture by conventional means. For example, the crude formula XXII product is isolated from the reaction mixture by acidification (e.g., acetic acid) and concentration under reduced pressure. Additionally, silica gel chromatographic separation is employed.

The formula XXII product is then converted to the formula XXIII product by dehydrohalogenation when $Y_1$ is $-C\equiv C-$. Dehydrohalogenation proceeds by conventional methods, e.g., reaction of the formula XXII product with base. An especially convenient base for this purpose is potassium t-butoxide. Thereafter, the formula XXIII product is transformed to the corresponding formula XXIV primary alcohol by selective hydrolysis of the silyl ether. For this purpose, dry tetrahydrofuran in tetra-n-butyl ammonium fluoride is employed in the manner known in the art for an hydrolysis of this type. Thereafter, the formula XXV carboxylic acid is prepared by oxidation of the primary alcohol. This oxidation is performed either in one step employing the Jones reagent or is optionally undertaken as a two-step oxidation, first preparing the corresponding aldehyde with a Collins reagent and thereafter oxidizing the aldehyde with silver oxide.

The formula XXVI product is then prepared either from the formula XXV compound (when $X_1$ is not $CH_2OH$) or the formula XXIII product (when $X_1$ is $-CH_2OH$). In preparing the formula XXVI product from the formula XXIII compound, hydrolysis of the silyl and tetrahydropyranyl ethers is undertaken by acidic means (e.g., employing mixtures of acetic acid, water and tetrahydrofuran as is known in the art). In preparing the formula XXVI compound from the formula XXV compound, the tetrahydropyranyl ethers of the formula XXV compound are first hydrolyzed, as described above, and thereafter the carboxyl group is optionally transformed to the corresponding ester, salt, or amide, according to the formula XXVI product desired.

The pharmacologically acceptable salts of these carboxylic acids are then obtained by neutralization with a corresponding base. Conventional techniques of isolation and recovery of the salt are employed.

With respect to the novel PG-type amides ($X_1$ is $-COL_4$) and esters, especially p-substituted phenyl esters ($R_1$ is p-substituted phenyl, such compounds are prepared as follows:

With regard to the preparation of the esters, especially p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amido and cycloamido derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PG-type carboxylic acids, the corresponding carboxyamides are then prepared by one of several amidation methods known in the prior art. See, for example, U.S. Pat. No. 3,981,868, issued Sept. 21, 1976, for a description of the preparation of the present amido and cycloamido derivatives of prostaglandin-type free acids and U.S. Pat. No. 3,954,741, describing the preparation of carbonylamido and sulfonylamido derivatives of prostaglandin-type free acids.

The preferred method by which the present amido and cycloamido derivatives of the novel prostacyclin-type free acids are prepared is, first by transformation of such free acids to corresponding mixed acid anhydrides. By this procedure, the prostaglandin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGF-type free acid is mixed with both the tertiary amine base and the chloroformate in a suitable solvent (e.g., aqueous tetrahydrofuran), allowing the reaction to proceed at −10° to 20° C.

Thereafter, the mixed anhydride is converted to the corresponding amido or cycloamido derivative by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about −10° to +10° C., until the reaction is shown to be complete. For highly volatile amines, acid addition salts thereof (e.g., methylamine hydrochloride) are employed in place of the corresponding free base (e.g., methylamine).

Thereafter, the novel PGF-type amido or cycloamido derivative is recovered from the reaction mixture by conventional techniques.

The carbonylamido and sulfonylamido derivatives of the presently disclosed PG-type compounds are likewise prepared by known methods. See, for example, U.S. Pat. No. 3,954,741 for description of the methods by which such derivatives are prepared. By this known method, the prostaglandin-type free acid is reacted with a carboxyacyl or sulfonyl isocyanate, corresponding to the carbonylamido or sulfonylamido derivative to be prepared.

By another, more preferred method the sulfonylamido derivatives of the present compounds are prepared by first generating the PG-type mixed anhydride, employing the method described above for the preparation of the amido and cycloamido derivatives. Thereafter, the sodium salt of the corresponding sulfonamide is reacted with the mixed anhydride and hexamethylphosphoramide. The pure PG-type sulfonylamido derivative is then obtained from the resulting reaction mixture by conventional techniques.

The sodium salt of the sulfonamide corresponding to the sulfonylamido derivative to be prepared is generated by reacting the sulfonamide with alcoholic sodium methoxide. Thus, by a preferred method, methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

With regard to the phenacyl or substituted phenacyl esters herein, see U.S. Pat. No. 3,979,440 for a description of their preparation.

DESCRIPTION OF THE PREFERRED EMBODIMENTS

The inention can be more fully understood by the following examples and preparations.

All temperatures are in degrees centigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer or an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-John or Thomas-Hoover melting point apparatus.

THF refers to tetrahydrofuran.

Specific Rotations, ($\alpha$), are determined for solutions of a compound in the specified solvent at ambient temperature with a Perkin-Elmer Model 141 Automatic Polarimeter.

Preparation 1: Dimethyl 2-oxo-5-t-butyldimethylsilyloxyphosphonate

A. Preparation of methyl-4-t-butyldimethylsilyloxybutanoate.

A sodium hydroxide solution (5.2 g in 50 ml of water) is added to a solution of butyrolactone (11.2 g) in 50 ml of water. The mixture is heated to 90° briefly, then allowed to cool to 25° and freeze-dried to give a white powder. The resulting sodium salt is stirred with 52 ml of dimethylformamide, t-butyldimethylsilyl chloride (19.6 g) and imidazole (17.7 g) are added. The mixture is then stirred overnight at 25°, then diluted with brine (520 ml) and extracted with 400 ml of 50% ether in Skellysolve B. The organic extracts are washed with cold 1N hydrochloric acid (130 ml) and brine (2 × 100 ml), then dried and evaporated to give 25.8 g as a colorless liquid. NMR (CDCl$_3$): 10.2, 3.8–3.52, 2.62–2.28, 2.1–1.55, and 0.88.

The acid thusly obtained is then esterified with diazomethane to give 27.3 g of an amber oil which is distilled to give 17.8 g of the product of this part as a colorless liquid, BP$_{0.4}$ is 58.5°–60°.

B. Preparation of dimethyl 2-oxo-5-t-butyldimethylsilyloxypentylphosphonate.

A solution of dimethyl methylphosphonate (21.8 g) in 140 ml of tetrahydrofuran is cooled to −75° and a solution of n-butyl lithium (99 ml, 1.77 M in hexane) is added slowly. The mixture is stirred for 20 min at −70° and then a solution of the reaction product of part A in tetrahydrofuran (17 ml + 5 ml rinse) added. Stirring is then continued for 3 hr at −70° and 16 hr at 25°. The reaction mixture is then cooled to 0°, acidified with acetic acid (10.3 ml, 180 mmol) and evaporated at reduced pressure. The residue is shaken with diethyl ether and water. The organic extracts are then washed with brine, dried and evaporated to give 28.1 g of yellow oil. Rapid distillation yields 23.4 g (93%) of title product, a colorless oil, BP$_{0.3}$ 115°–151° C. NMR (CCl$_4$): 3.76 and 3.58, 3.7–3.4, 3.12 and 2.75, 2.75–2.45, 1.95–1.40, 0.83, and 0.0.

Example 1: 2-Decarboxy-2-t-butyldimethylsilyloxymethyl-4-oxo-6α- and 6β-PGI$_1$, 11,15-bistetrahydropyranyl ether.

A solution of 13.8 g of dimethyl 2-oxo-5-t-butyldimethylsilyloxypentylphosphonate in tetrahydrofuran (35 ml) is added rapidly to a stirred suspension of sodium hydride (2.05 g, 50% in mineral oil) in 365 ml of dry tetrahydrofuran at 5°. The mixture is stirred for 1 hr at 5° and 1 hr at 25°. A resulting white slurry is then cooled to 5° and a solution of 18.7 g of 3α,5α-dihydroxy-2β-(3α-hydroxy-trans-1-octenyl)-1α-cyclopentanacetaldehyde, δ-lactol, bis(tetrahydropyranyl ether) in tetrahydrofuran (70 ml) is added. The mixture is stirred 2 hr at 5° and overnight at 25° to give a brown solution which was acidified with acetic acid (2.6 ml) and evaporated at reduced pressure. The residue is shaken with ethyl acetate and water. The organic extract is washed with 1N potassium bicarbonate and brine, then dried and evaporated to give 27.6 g of a thick yellow-brown oil. Chromatography on 2 kg of silica gel in 25% ethyl acetate-Skellysolve B (500 ml fractions) yields 23.8 g (88%) of title product as a yellow oil (fractions 16–28). NMR (CCl$_4$): 5.65–5.2, 4.75–3.1, 3.75–3.45, 0.86, and 0.0. IR (CH$_2$Cl$_2$): 1695, 985 cm$^{-1}$.

Example 2: 2-Decarboxy-2-hydroxymethyl-4-oxo-6α- and 6β-PGI$_1$.

A solution of 4.0 g of the title product of Example 1 in tetrahydrofuran (57 ml) and water (8 ml) is mixed with a solution of 41.5 g of citric acid in 41.5 ml of water and stirred for 2 hr at 31°. The mixture is then cooled to 15°, 1N potassium bicarbonate (104 ml) added and tetrahydrofuran evaporated at reduced pressure. The residue is extracted with ethyl acetate and the extracts washed to give 3.3 g of a colorless oil which by tlc (50% acetone-methylene chloride) contained a major polar spot (Rf 0.13) and numerous less polar materials. The oil is chromatographed on 200 g of silica gel in 50% acetone in methylene chloride (200 ml fractions) to give 1.99 g of thin yellow oil (fractions 2–9) and 1.2 g of a pale yellow oil (crystallized at +5°) in fractions 13–20. The latter fraction is crystallized from acetone-Skellysolve B and acetone to give 0.25 g of white crystals, MP 68°–69.5°, a mixture of the 6α- and 6β-title products. Elemental Analysis: C, 67.37, H, 9.65. MS (TMS): 570.3558 (high resolution peak) m/e: 555, 499, 480, 409, 173, 159.

Example 3: 2-Decarboxy-2-hydroxymethyl-4-oxo-6α- and 6β-PGI$_1$, 11,15-bistetrahydropyranyl ether.

A solution of 11.9 g of the title product of Example 1 in 75 ml of dry tetrahydrofuran and a solution of tetra-n-butylammonium fluoride (36 ml 1.3M in THF) is stirred at 25° for 20 min. The reaction mixture is poured into a mixture of brine (30 ml), 1N potassium bicarbonate (190 ml) and ethyl acetate (190 ml). The organic layer is washed 2 × 300 ml with brine and aqueous layers backwashed (2 × 300 ml) with ethyl acetate.

The resulting extract is dried and evaporated to give 11.98 g of a brown oil which is chromatographed on 1 kg of silica gel in 20% acetone in methylene chloride. Elution (500 ml fractions) with 8 l of 20% to 35% acetone in methylene chloride yields 9.0 g of pure title product (fractions 11–17).

Example 4: 2-Decarboxy-2-oxomethyl-4-oxo-6α- and 6β-PGI$_1$, 11,15-bistetrahydropyranyl ether.

A mixture of pyridine (19.5 ml, 241.4 mmol) and chomium trioxide (12.1 g, 121 mmol) in 290 ml of methylene chloride is stirred for 15 min. A solution of 9.8 g (19.9 mmol) of the title product of Example 3 in methylene chloride (100 ml) is added. The mixture is then stirred for 0.5 hr and rinsed into a beaker containing diatomaceous earth, 200 ml of ice and 250 ml of 1N potassium bisulfate. The mixture is stirred 10 min then filtered through the diatomaceous earth wet with methylene chloride. The filter cake is washed with a total of 400 ml of methylene chloride. The organic layer is washed 2 × 200 ml with water and filtered through sodium sulfate. The aqueous layer is re-extracted with 400 ml and 200 ml of methylene chloride. The combined extracts are evaporated at reduced pressure to give a dark brown oil which is immediately chromatographed on 500 g of silica gel in 25% acetone in methylene chloride (500 ml fractions) to give 8.6 g (87%) of title aldehyde as a pale amber oil (fractions 3–5). NMR (CDCl$_3$): 9.78, 5.75–5.3, 4.85–3.2, and 2.75.

Example 5: 4-Oxo-6α- and 6β-PGI$_1$, 11,15-bistetrahydropyranyl ether.

To a solution of 8.62 g of the title product of Example 4 in 84 ml of 95% ethanol is added to 6.25 g of silver nitrate in 11 ml of water. The mixture is stirred at 20° while a solution of potassium hydroxide (5.0 g in 84 ml of water) is added over a period of 10 min. Stirring is continued for 2 hr at 25°. The reaction mixture is then filtered through diatomaceous earth (wet with water), and the filter cake washed with a total of 170 ml of water. The aqueous layer is then washed twice with diethyl ether, then cooled to 10°, acidified with potassium bisulfate (11.2 g) and extracted (3 × 150 ml) with ethyl acetate. The organic extracts are then washed with brine, dried and evaporated at reduced pressure to give 8.5 g (95%) of pure title product as a thick yellow oil.

Example 6: 4-Oxo-6α-PGI$_1$, methyl ester, and 4-oxo-6β-PGI$_1$, methyl ester.

A solution of 8.5 g of the title product of Example 5 in 130 ml of diethyl ether is esterified with diazomethane. The residue is dissolved in 470 ml of tetrahydrofuran, water, and acetic acid (1:3:6), allowed to stand at 40° for 4 hr, then diluted with 940 ml of water and lyophilized. The residue is shaken with 300 ml of ethyl acetate and 50 ml of 1M sodium carbonate and the basic aqueous layer extracted with ethyl acetate. The organic extracts are washed with brine, dried and evaporated at reduced pressure to give 9.9 g of a thick yellow oil which was chromatographed on 500 g of silica gel in 40% acetone in methylene chloride (500 ml fractions). Fraction 6–13 contains 5.1 g of yellow oil and crystals, mainly a mixture of 6α- and 6β-PGI$_1$, methyl ester.

A 3.2 g sample of the mixture is chromatographed on 150 g of silica gel in 50% acetone in hexane (50 ml fractions), yielding

| Fractions | 6β-isomer | 6α-isomer | (X) |
|---|---|---|---|
| 35–37 | — | 0.28 g | 0.03 g |
| 38–47 | 1.05 g | 0.56 g | |
| 48–64 | 1.17 g | 0.05 g | |

Fractions 48–64 are crystallized twice from ether-pentane to give 0.67 g of the 6β-isomer as white crystals, MP 67.5°–68°. Elemental Analysis: C, 65.61; H, 9.02. MS(TMS): 526.3165 (high resolution peak) m/e: 511, 455, 436, 397, 365, 173, and 115. IR (mull): 3460, 1735, 1715, 1335, 1315, 1275, 1210, 1085, 1065, 1020, 970 cm$^{-1}$.

Fractions 35–47 were combined and rechromatographed on silica columns in series, packed in 50% acetone in hexane. Elution (25 ml fractions) gave 0.62 g of nearly pure 6α-isomer in fractions 33–38. Crystallization from acetone-hexane gave 0.30 g of pure 6α-isomer as a white powder, MP 83°–85°, still containing a trace of slightly less polar impurity. Elemental Analysis: C, 65.94; H, 9.16. MS(TMS): 526.3113 (high resolution peak). IR (mull): 3500, 3420, 1740, 1725, 1710, 1675, 1085, 1060, 1020, 980, 970, 890 cm$^{-1}$.

Example 7: 4-Oxo-6β-PGI$_1$.

A 1.8 g sample of a mixture of 6α- and 6β-4-oxo-PGI$_1$, methyl ester in 80 ml of 95% ethanol and 16 ml of 1N sodium hydroxide is allowed to stand for 2.5 hr. The crude acid product obtained is chromatographed on 150 g of acid washed silica gel in 30% acetone-methylene chloride. Elution (50 ml fractions) with 5 l of 30% to 70% acetone-methylene chloride yields enrichment of the more polar epimer in fractions 54–79. Two crystallizations from acetone yields 0.57 g of the title isomer as white crystals, MP 114.8°–115.8°. TIC (A-IX) showed that about 15% of the less polar epimer was still present. Elemental Analysis: C, 65.69, 65.55; H, 9.17, 8.92. MS(TMS): 584.3352 (high resolution peak) m/e: 569, 513, 494, 479, 439, 423, 378, and 173.

Further, following the procedures described above there is prepared the corresponding PGI$_1$-type, amides, prepared by methods described above. Further, for the above carboxylic acids, the corresponding pharmacologically acceptable salts are prepared by neutralization with the appropriate base.

Following the procedure of the above examples, but employing the appropriate lactol starting material, there are prepared 4-oxo-6α-PGI$_1$-type compounds;
4-oxo-6β-PGI$_1$-type compounds;
11-deoxy-4-oxo-6α-PGI$_1$-type compounds;
11-deoxy-4-oxo-6β-PGI$_1$-type compounds;
11-deoxy-11-hydroxymethyl-4-oxo-6α-PGI$_1$-type compounds;
11-deoxy-11-hydroxymethyl-4-oxo-6β-PGI$_1$-type compounds;
7a-homo-6α-PGI$_1$-type compounds;
7a-homo-6β-PGI$_1$-type compounds;
7a-homo-11-deoxy-4-oxo-6α-PGI$_1$-type compounds;
7a-homo-11-deoxy-4-oxo-6β-PGI$_1$-type compounds;
7a-homo-11-deoxy-11-hydroxymethyl-4-oxo-6α-PGI$_1$-type compounds; or
7a-homo-11-deoxy-11-hydroxymethyl-4-oxo-6β-PGI$_1$-type compounds;

in free acid, primary alcohol, or ester form which exhibit the following side chain substituents:

15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;

17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-Phenoxy-18,19,20-trinor-13-cis-;
16-Methyl-16-phenoxy-18,19,20-trinor-13-cis-;
2a,2b-Dihomo-;
2a,2b-Dihomo-15-methyl-;
2a,2b-Dihomo-16-methyl-;
2a,2b-Dihomo-16,16-dimethyl-;
2a,2b-Dihomo-16-fluoro-;
2a,2b-Dihomo-16,16-difluoro-;
2a,2b-Dihomo-17-phenyl-18,19,20-trinor-;
2a,2b-Dihomo-17-(m-trifluoromethylphenyl)-18,19,20-trinor-;
2a,2b-Dihomo-17-(m-chlorophenyl)-18,19,20-trinor-;
2a,2b-Dihomo-17-(p-fluorophenyl)-18,19,20-trinor-;
2a,2b-Dihomo-16-methyl-17-18,19,20-trinor-;
2a,2b-Dihomo-16,16-dimethyl-17-phenyl-18,19,20-trinor-;
2a,2b-Dihomo-16-fluoro-17-phenyl-18,19,20-trinor-;
2a,2b-Dihomo-16,16-difluoro-17-phenyl-18,19,20-trinor-;
2a,2b-Dihomo-16-phenyl-17,18,19,20-tetranor-;
2a,2b-Dihomo-16-(m-trifluoromethylphenyl)-17,18,19,20-tetranor-;
2a,2b-Dihomo-16-(m-chlorophenyl)-17,18,19,20-tetranor-;
2a,2b-Dihomo-16-(p-fluorophenyl)-17,18,19,20-tetranor-;
2a,2b-Dihomo-16-phenyl-18,19,20-trinor-;
2a,2b-Dihomo-16-methyl-16-phenyl-18,19,20-trinor-;
2a,2b-Dihomo-16-phenoxy-17,18,19,20-tetranor-;
2a,2b-Dihomo-16-(m-trifluoromethylphenoxy)-17,18,19,20-tetranor-;
2a,2b-Dihomo-16-(m-chlorophenoxy)-17,18,19,20-tetranor-;
2a,2b-Dihomo-16-(p-fluorophenoxy)-17,18,19,20-tetranor-;
2a,2b-Dihomo-16-phenoxy-18,19,20-trinor-;
2a,2b-Dihomo-16-methyl-16-phenoxy-18,19,20-trinor-;
2a,2b-Dihomo-16-methyl-13,14-didehydro-;
2a,2b-Dihomo-16,16-dimethyl-13,14-didehydro-;
2a,2b-Dihomo-16-fluoro-13,14-didehydro-;
2a,2b-Dihomo-16,16-difluoro-13,14-didehydro-;
2a,2b-Dihomo-17-phenyl-18,19,20-trinor-13,14-didehydro-;
2a,2b-Dihomo-17-(m-trifluoromethylphenyl)-18,19,20-trinor-13,14-didehydro-;
2a,2b-Dihomo-17-(m-chlorophenyl)-18,19,20-trinor-13,14-didehydro-;
2a,2b-Dihomo-17-(p-fluorophenyl)-18,19,20-trinor-13,14-didehydro-;
2a,2b-Dihomo-16-methyl-17-phenyl-18,19,20-trinor-13,14-didehydro-;
2a,2b-Dihomo-16,16-dimethyl-17-phenyl-18,19,20-trinor-13,14-didehydro-;
2a,2b-Dihomo-16-fluoro-17-phenyl-18,19,20-trinor-13,14-didehydro-;
2a,2b-Dihomo-16,16-Difluoro-17-phenyl-18,19,20-trinor-13,14-didehydro-;
2a,2b-Dihomo-16-phenyl-17,18,19,20-tetranor-13,14-didehydro-;
2a,2b-Dihomo-16-(m-trifluoromethylphenyl)-17,18,19,20-tetranor-13,14-didehydro-;
2a,2b-Dihomo-16-(m-chlorophenyl)-17,18,19,20-tetranor-13,14-didehydro-;
2a,2b-Dihomo-16-phenyl-18,19,20-trinor-13,14-didehydro-;
2a,2b-Dihomo-16-methyl-16-phenyl-18,19,20-trinor-13,14-didehydro-;
2a,2b-Dihomo-16-phenoxy-17,18,19,20-tetranor-13,14-didehydro-;
2a,2b-Dihomo-16-(m-trifluoromethylphenoxy)-17,18,19,20-tetranor-13,14-didehydro-;
2a,2b-Dihomo-16-(m-chlorophenoxy)-17,18,19,20-tetranor-13,14-didehydro-;
2a,2b-Dihomo-16-phenoxy-18,19,20-trinor-13,14-didehydro-;
2a,2b-Dihomo-16-methyl-16-phenoxy-18,19,20-trinor-13,14-didehydro-;
2a,2b-Dihomo-13,14-dihydro-;
2a,2b-Dihomo-16-methyl-13,14-dihydro-;
2a,2b-Dihomo-16,16-dimethyl-13,14-dihydro-;

2a,2b-Dihomo-16-fluoro-13,14-dihydro-;
2a,2b-Dihomo-16,16-difluoro-13,14-dihydro-;
2a,2b-Dihomo-17-phenyl-18,19,20-trinor-13,14-dihydro-;
2a,2b-Dihomo-17-(m-trifluoromethylphenyl)-18,19,20-trinor-13,14-dihydro-;
2a,2b-Dihomo-17-(m-chlorophenyl)-18,19,20-trinor-13,14-dihydro-;
2a,2b-Dihomo-17-(p-fluorophenyl)-18,19,20-trinor-13,14-dihydro-;
2a,2b-Dihomo-16-methyl-17-phenyl-18,19,20-trinor-13,14-dihydro-;
2a,2b-Dihomo-16,16-dimethyl-17-phenyl-18,19,20-trinor-13,14-dihydro-;
2a,2b-Dihomo-16-fluoro-17-phenyl-18,19,20-trinor-13,14-dihydro-;
2a,2b-Dihomo-16,16-difluoro-17-phenyl-18,19,20-trinor-13,14-dihydro-;
2a,2b-Dihomo-16-phenyl-17,18,19,20-tetranor-13,14-dihydro-;
2a,2b-Dihomo-16-(m-trifluoromethylphenyl)-17,18,19,20-tetranor-13,14-dihydro-;
2a,2b-Dihomo-16-(m-chlorophenyl)-17,18,19,20-tetranor-13,14-dihydro-;
2a,2b-Dihomo-16-(p-fluorophenyl)-17,18,19,20-tetranor-13,14-dihydro-;
2a,2b-Dihomo-16-phenyl-18,19,20-trinor-13,14-dihydro-;
2a,2b-Dihomo-16-methyl-16-phenyl-18,19,20-trinor-13,14-dihydro-;
2a,2b-Dihomo-16-phenoxy-17,18,19,20-tetranor-13,14-dihydro-;
2a,2b-Dihomo-16-(m-trifluoromethylphenoxy)-17,18,19,20-tetranor-13,14-dihydro-;
2a,2b-Dihomo-16-(m-chlorophenoxy)-17,18,19,20-tetranor-13,14-dihydro-;
2a,2b-Dihomo-16-(p-fluorophenoxy)-17,18,19,20-tetranor-13,14-dihydro-;
2a,2b-Dihomo-16-phenoxy-18,19,20-trinor-13,14-dihydro-;
2a,2b-Dihomo-16-methyl-16-phenoxy-18,19,20-trinor-13,14-dihydro-;
2a,2b-Dihomo-13-cis-;
2a,2b-Dihomo-16-methyl-13-cis-;
2a,2b-Dihomo-16,16-dimethyl-13-cis-;
2a,2b-Dihomo-16-fluoro-13-cis-;
2a,2b-Dihomo-16,16-difluoro-13-cis-;
2a,2b-Dihomo-17-phenyl-18,19,20-trinor-13-cis-;
2a,2b-Dihomo-17-(m-trifluoromethylphenyl)-18,19,20-trinor-13-cis-;
2a,2b-Dihomo-17-(m-chlorophenyl)-18,19,20-trinor-13-cis-;
2a,2b-Dihomo-17-(p-fluorophenyl)-18,19,20-trinor-13-cis-;
2a,2b-Dihomo-16-methyl-17-phenyl-18,19,20-trinor-13-cis-;
2a,2b-Dihomo-16,16-dimethyl-17-phenyl-18,19,20-trinor-13-cis-;
2a,2b-Dihomo-16-fluoro-17-phenyl-18,19,20-trinor-13-cis-;
2a,2b-Dihomo-16,16-difluoro-17-phenyl-18,19,20-trinor-13-cis-;
2a,2b-Dihomo-16-phenyl-17,18,19,20-tetranor-13-cis-;
2a,2b-Dihomo-16-(m-trifluoromethylphenyl)-17,18,19,20-tetranor-13-cis-;
2a,2b-Dihomo-16-(m-chlorophenyl)-17,18,19,20-tetranor-13-cis-;
2a,2b-Dihomo-16-(p-fluorophenyl)-17,18,19,20-tetranor-13-cis-;
2a,2b-Dihomo-16-phenyl-18,19,20-trinor-13-cis-;
2a,2b-Dihomo-16-methyl-16-phenyl-18,19,20-trinor-13-cis-;
2a,2b-Dihomo-16-phenoxy-17,18,19,20-tetranor-13-cis-;
2a,2b-Dihomo-16-(m-trifluoromethylphenoxy)-17,18,19,20-tetranor-13-cis-;
2a,2b-Dihomo-16-(m-chlorophenoxy)-17,18,19,20-tetranor-13-cis-;
2a,2b-Dihomo-16-(p-fluorophenoxy)-17,18,19,20-tetranor-13-cis-;
2a,2b-Dihomo-16-phenoxy-18,19,20-trinor-13-cis-; and
2a,2b-Dihomo-16-methyl-16-phenoxy-18,19,20-trinor-13-cis-.

I claim:

1. A prostacyclin analog of the formula

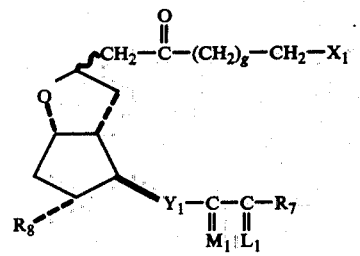

wherein $g$ is the integer one, 2, or 3;
wherein $R_8$ is hydrogen, hydroxy, or hydroxymethyl;
wherein $Y_1$ is
(1) trans—CH=CH—,
(2) cis—CH=CH—,
(3) —CH$_2$CH$_2$—, or
(4) —C≡C—,
wherein $M_1$ is

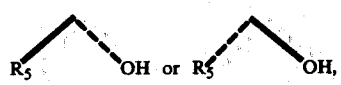

wherein $R_5$ is hydrogen or alkyl with one to 4 carbon atoms, inclusive,
wherein $L_1$ is

or a mixture of

wherein $R_3$ and $R_4$ are hydrogen, methyl, or fluoro, being the same or different, with the proviso that one of $R_3$ and $R_4$ is fluoro only when the other is hydrogen or fluoro;
wherein $X_1$ is
(1) —COOR$_1$ wherein $R_1$ is hydrogen; alkyl of one to 12 carbon atoms, inclusive; cycloalkyl of 3 to 10 carbon atoms, inclusive, hydrocarbylaralkyl of 7 to 12 carbon atoms, inclusive; phenyl; phenyl substituted with one, two, or three chloro or alkyl of one to 3 carbon atoms; phenyl substituted in the para position by

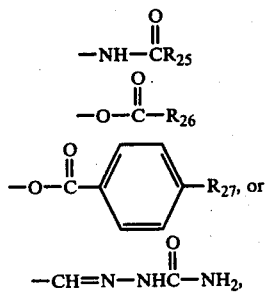

wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is hydrogen or acetamido; inclusive, phenacyl, i.e.,

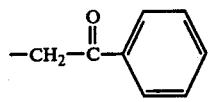

phenacyl substituted in the para position by chloro, bromo, phenyl, or benzamido; or a pharmacologically acceptable cation;

(2) —$CH_2OH$; or (3) —$COL_4$, wherein $L_4$ is
(a) amino of the formula —$NR_{21}R_{22}$; wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive, hydroxy, carboxy, alkoxycarbonyl of one to 4 carbon atoms, inclusive, or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro; pyridyl; pyridyl substituted by one, 2, or 3 chloro, alkyl of one to 3 carbon atoms, inclusive, or alkoxy of one to 3 carbon atoms, inclusive; pyridylalkyl of one to 4 carbon atoms, inclusive; pyridylalkyl substituted by one, 2, or 3 chloro, alkyl of one to 3 carbon atoms, inclusive, hydroxy, or alkoxy of one to 3 carbon atoms, inclusive; hydroxyalkyl of one to 4 carbon atoms, inclusive; dihydroxyalkyl of one to 4 carbon atoms; and trihydroxyalkyl of one to 4 carbon atoms; with the further proviso that not more than one of $R_{21}$ and $R_{22}$ is other than hydrogen or alkyl;

(b) cycloamino selected from the group consisting of

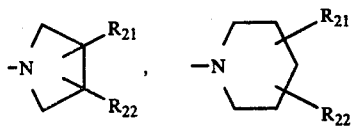

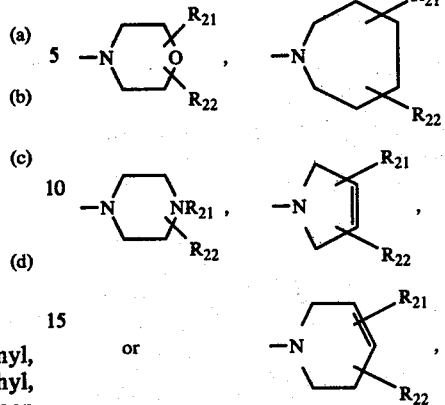

wherein $R_{21}$ and $R_{22}$ are as defined above;

(c) carbonylamino of the formula —$NR_{23}COR_{21}$, wherein $R_{23}$ is hydrogen or alkyl of one to 4 carbon atoms and $R_{21}$ is as defined above;

(d) sulfonylamino of the formula —$NR_{23}SO_2R_{21}$, wherein $R_{21}$ and $R_{23}$ are as defined above; or (e) hydrazino of the formula —$NR_{23}R_{24}$, wherein $R_{23}$ is as defined above and $R_{24}$ is amino of the formula —$NR_{21}R_{22}$, as defined above, or cycloamino, as defined above; and wherein $R_7$ is (1) —$(CH_2)_m$—$CH_3$;

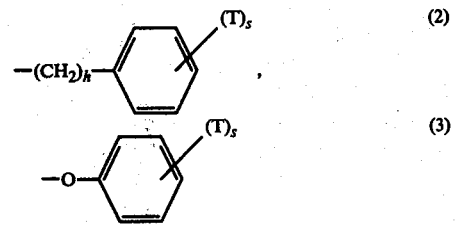

wherein $m$ is the integer one to 5, inclusive, $h$ is the integer zero to 3, inclusive; $s$ is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. A prostacyclin analog according to claim 1, wherein $R_8$ is hydroxymethyl.

3. 11-Deoxy-11α-hydroxymethyl-4-oxo-6α- or 6β-$PGI_1$, a prostacyclin analog according to claim 2.

4. A prostacyclin analog according to claim 1, wherein $R_8$ is hydrogen.

5. 11-Deoxy-4-oxo-6α- or 6β-$PGI_1$, a prostacyclin analog according to claim 4.

6. A prostacyclin analog according to claim 1, wherein $R_8$ is hydroxy.

7. A prostacyclin analog according to claim 6, wherein $Y_1$ is cis—CH=CH—, —C≡C—, or —$CH_2CH_2$—.

8. cis-13-4-Oxo-$PGI_1$, a prostacyclin analog according to claim 7.

9. 13,14-Didehydro-4-oxo-6α- or 6β-$PGI_1$, a prostacyclin analog according to claim 7.

10. 13,14-Dihydro-4-oxo-6α- or 6β-$PGI_1$, a prostacyclin analog according to claim 7.

11. A prostacyclin analog according to claim 6, wherein $Y_1$ is trans—CH=CH—.

12. A prostacyclin analog acording to claim 11, wherein the C-6 side chain is a mixture of alpha and beta isomers.

13. (6RS)-4-Oxo-PGI$_1$, a prostacyclin analog according to claim 12.

14. A prostacyclin analog according to claim 11, wherein the C-6 side chain is in the alpha configuration.

15. 4-Oxo-6α-PGI$_1$, a prostacyclin analog according to claim 14.

16. A prostacyclin analog according to claim 11, wherein the C-6 side chain is in the beta configuration.

17. A prostacyclin analog according to claim 16, wherein g is two.

18. 2a-Homo-4-oxo-6β-PGI$_1$, a prostacyclin analog according to claim 17.

19. A prostacyclin analog according to claim 16, wherein g is one or 3.

20. A prostacyclin analog according to claim 19, wherein g is one.

21. A prostacyclin analog according to claim 20, wherein $R_7$ is

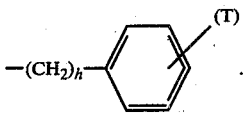

22. 17-Phenyl-18,19,20-trinor-4-oxo-6β-PGI$_1$, a prostacyclin analog according to claim 21.

23. A prostacyclin analog according to claim 20, wherein $R_7$ is

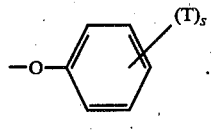

24. 16-Phenoxy-17,18,19,20-tetranor-4-oxo-6β-PGI$_1$, a prostacyclin analog according to claim 23.

25. A prostacyclin analog according to claim 20, wherein $R_7$ is —(CH$_2$)$_m$—CH$_3$—.

26. A prostacyclin analog according to claim 25, wherein m is 3.

27. A prostacyclin analog according to claim 26, wherein $X_1$ is —COL$_4$.

28. 4-Oxo-6β-PGI$_1$, amide, a prostacyclin analog according to claim 27.

29. A prostacyclin analog according to claim 27, wherein $X_1$ is —CH$_2$OH.

30. 2-Decarboxy-2-hydroxymethyl-4-oxo-6β-PGI$_1$, a prostacyclin analog according to claim 29.

31. A prostacyclin analog according to claim 26, wherein $X_1$ is —COOR$_1$.

32. A prostacyclin analog according to claim 31, wherein $R_5$ is methyl.

33. 15-Methyl-4-oxo-6β-PGI$_1$, a prostacyclin analog according to claim 32.

34. A prostacyclin analog according to claim 31, wherein $R_5$ is hydrogen.

35. A prostacyclin analog according to claim 34, wherein at least one of $R_3$ and $R_4$ is fluoro.

36. 16,16-Difluoro-4-oxo-6β-PGI$_1$, a prostacyclin analog according to claim 35.

37. A prostacyclin analog according to claim 34, wherein at least one of $R_3$ and $R_4$ is methyl.

38. 16,16-Dimethyl-4-oxo-6β-PGI$_1$, a prostacyclin analog according to claim 37.

39. A prostacyclin analog according to claim 34, wherein $R_3$ and $R_4$ are both hydrogen.

40. 4-Oxo-6β-PGI$_1$, methyl ester, a prostacyclin analog according to claim 39.

41. 4-Oxo-6β-PGI$_1$-tris(hydroxymethyl)amino methane salt, a prostacyclin analog according to claim 39.

42. 4-Oxo-6β-PGI$_1$, adamantanamine salt, a prostacyclin analog according to claim 39.

43. 4-Oxo-6β-PGI$_1$, a prostacyclin analog according to claim 39.

* * * * *

UNITED STATES PATENT AND TRADEMARK OFFICE
CERTIFICATE OF CORRECTION

PATENT NO. : 4,126,744
DATED : November 21, 1978
INVENTOR(S) : Donald E. Ayer

It is certified that error appears in the above—identified patent and that said Letters Patent is hereby corrected as shown below:

Column 1, lines 48-54, should appear as follows:

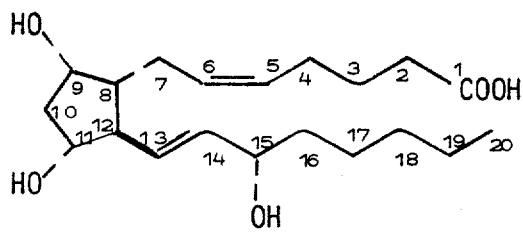

Column 5, line 25, "$R_{21}$ and $R_{22}$ are" should read -- $R_{21}$ and $R_{23}$ are --;

Column 19, line 54, "inention" should read -- invention --.

Signed and Sealed this

Eighth Day of December 1981

[SEAL]

Attest:

Attesting Officer

GERALD J. MOSSINGHOFF
Commissioner of Patents and Trademarks